(12) United States Patent
Kawai et al.

(10) Patent No.: US 6,534,268 B1
(45) Date of Patent: Mar. 18, 2003

(54) HUMAN BMP-7 PROMOTER AND METHOD FOR EXPLORING BONE-RELATED SUBSTANCE BY USING THE SAME

(75) Inventors: Shinji Kawai, Paris (FR); Takeyuki Sugiura, Tokyo (JP)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 09/674,311

(22) PCT Filed: Apr. 22, 1999

(86) PCT No.: PCT/IB99/00733

§ 371 (c)(1),
(2), (4) Date: Nov. 30, 2000

(87) PCT Pub. No.: WO99/57293

PCT Pub. Date: Nov. 11, 1999

(30) Foreign Application Priority Data

Apr. 30, 1998 (JP) ............................................. 10-120174

(51) Int. Cl.[7] ........................... C12Q 1/68; C12P 19/34; C12N 15/63; C07H 21/02; C07H 21/04
(52) U.S. Cl. ........................... 435/6; 435/91.1; 435/455; 536/23.1; 536/24.1
(58) Field of Search ............................... 536/23.1, 24.1; 435/320.1, 91.2, 91.4

(56) References Cited

U.S. PATENT DOCUMENTS 5,468,845 A    11/1995  Oppermann et al.
5,650,276 A  *  7/1997  Smart et al. ................... 435/6

FOREIGN PATENT DOCUMENTS

| WO | 9011366 | 10/1990 |
| WO | 9533831 | 12/1995 |
| WO | 9638590 | 12/1996 |
| WO | 9823740 |  6/1998 |
| WO | 9854355 | 12/1998 |

OTHER PUBLICATIONS

New England Biolabs, Inc. pp. 60–62.*
Biochemical & Biophysical Res. Comm.vol. 221, No. 3 1996.

* cited by examiner

*Primary Examiner*—Sean McGarry
*Assistant Examiner*—Jane Zara
(74) *Attorney, Agent, or Firm*—Bierman, Muserlian and Lucas (57) ABSTRACT

The present invention provides a method for exploring low molecular weight compounds which regulate positively or negatively the expression of human BMP-7 with reference to a reporter activity by using 5' upstream region gene containing the human BMP-7 promoter and an animal cell introduced with the vector that has been connected to an appropriate reporter gene. The low molecular weight compounds and their derivatives obtained by the present method have morphogenetic activity or inhibiting activity for bone and cartilage through the expression of the human BMP-7 and are useful as preventive or therapeutic agents for cartilage and bone diseases. Furthermore, the low molecular weight compounds and their derivatives are useful as therapeutic agents for kidney diseases.

4 Claims, 3 Drawing Sheets

HUMAN BMP-7 PROMOTER AND METHOD FOR EXPLORING BONE-RELATED SUBSTANCE BY USING THE SAME

This application is a 371 of PCT/IB99/00733 filed Apr. 22, 1999.

BACKGROUND OF THE INVENTION

(1) Field of the Invention

The present invention relates to a 5' upstream region DNA containing a promoter of a human bone morphogenetic protein (hereafter referred to as BMP-7). Further, the present invention relates to a method for exploring a low molecular weight compound positively or negatively which regulates the expression of human BMP-7 by using a mass of animal or yeast cells that are introduced with a recombinant expression vector harboring a 5' upstream region DNA containing the human BMP-7 promoter integrated into a suitable reporter gene, and by using a reporter activity as an indicator.

(2) Description of the Related Art

At present, a bone morphogenetic activity has been reported for a bone morphogenetic factor, BMP, belonging to TGF (transforming growth factor) -β superfamily (Science 150, 893–897, 1965; Science 242, 1528–1534, 1988). Known species of BMP are BMP-1 to BMP-14. Among them, the members from BMP-2 to BMP-14 have been known as showing the bone morphogenetic activity. BMPs ranging from BMP-2 to BMP-14 are considered as effective to therapeutic and preventive treatment for various bone dysfunction and bone diseases, however, they exist in very small amount in nature. Therefore, an available large quantity from BMP-2 to BMP-14 used for these treatments requires production of recombinant protein. The production of the recombinant protein generally is very expensive compared with a low molecular weight compound. Furthermore, there are many restrictions as a medical drug in terms of physical properties and administration methods due to proteinic characteristics. Considering these points, a small molecular organic compound having the activity equal to that of the BMP protein, if any, should be a highly promising medical drug. The substance obtainable with the exploring method provided by the present invention has the activity to induce the expression of human BMP-7, a bone osteogenesis factor, and also has the efficacy equal to that of human BMP-7, representing very high usefulness. On the contrary, if human BMP-7 is concerned with bone and cartilage hyperplasia, inhibiting the expression may prevent osteohyperplasia. The present invention is able to detect the inhibition of the human BMP-7 expression and provides a method for exploring a substance to prevent hyperplasia. In addition, it is known that human BMP-7 has the ability to enhance the differentiation of kidney cells (Proc. Natnl. Acad. Sci., U.S.A., Vol. 93, p. 9021–9026, 1996). Thus, the experimental system provided by the present invention can be applied to a method for exploring the agent for the treatment of the kidney disorder.

For such an exploring method, an example has been so far only reported using a murine BMP-2 promoter (WO97/15308), and there is no example of using the human BMP-7 promoter. In addition, since the materials of the exploring method provided by the present invention are all derived from human sources, it can be expected that discovered substances should show the effects at clinic practically.

SUMMARY OF THE INVENTION

The present invention provides a 5' upstream region DNA containing a promoter of human BMP-7. By using 5' upstream region gene containing the human BMP-7 promoter and an animal cell introduced with a recombinant expression vector that has been connected to an appropriate reporter gene, the low molecular weight compounds which regulate positively or negatively the expression of human BMP-7 can be explored with reference to a reporter activity. The low molecular weight compounds and their derivatives have morphogenetic activity and inhibiting activity for bone and cartilage through the expression of human BMP-7 and are effective as preventive or therapeutic agents for cartilage and bone diseases, remedies for osteometastasis, or therapeutic and preventive agents for excess osteogenesis. Furthermore, these low molecular weight compounds and their derivatives are useful as preventive or therapeutic agents for kidney disorders.

DESCRIPTION OF THE PREFERRED EMBODIMENT

The present invention relates to a DNA whose nucleotide sequence is represented by the base sequence No. from 1 to 10877 shown in SEQ ID NO. 1 of the Sequence Listing that encodes a human bone morphogenetic protein-7 promoter region, or a fragment thereof. SEQ ID NO. 1 of the Sequence Listing shows the 5' upstream region sequence of the human BMP-7 gene.

The present invention relates to a method for preparing the DNA shown in SEQ ID NO. 1 of the Sequence Listing by conducting the steps of:

(1) digestion of a human placenta genomic DNA with a HindIII restriction enzyme, (2) isolation by agarose gel electrophoresis, (3) cloning of the isolated DNA fragment digested with HindIII into a lambda phage vector λDASH II treated with the same enzyme, (4) packaging of said vector into the phage, (5) establishment of genomic DNA library by infecting *Escherichia coli* with the phage, (6) screening by PCR, and (7) subcloning into a plasmid vector.

The plasmid vector used herewith is not restricted and can be used among ones commercialized. A pUC18 vector can be a preferable example.

The present invention relates to a recombinant expression vector characterized by integration of the full length or a part of DNA shown in SEQ ID NO. 1 of the Sequence Listing into a reporter gene. In detail, the recombinant expression vector is constructed to locate a suitable region of 5' upstream region of the human BMP-7 gene, that is represented by SEQ ID NO. 1 of the Sequence Listing, in front of a reporter gene. The reporter gene such as luciferase or β-galactosidase gene shows an expressing status on behalf an original product. The vector as the original for the recombination expression vector is not specially restricted to allow to use a plasmid vector commercialized. The present invention used pGL3-basic as a preferable example. The use of pGL3-basic yielded pMSS115 (9.2 kb) that is a recombination expression vector containing the human BMP-7 promoter and a luciferase gene. The present invention assigned it to the recombination expression vector. It is necessary to introduce the vector to mammalian cells, preferably a human osteoblast-like cells, such as SaOS-2 cells, with a liposome. The animal cells stably transfected with the recombinant expression vector are selected by using a resistance marker.

The present invention relates to a method for exploring a bone-related substance, characterized by using the recombinant expression vector characterized by integration of the full length or a part of DNA shown in SEQ ID NO. 1 of the Sequence Listing into a reporter gene. It relates to the method for exploring a bone-related substance wherein the bone-related substance is osteogenesis inducing substance or a bone-related substance wherein a bone-related substance is osteogenesis inhibiting substance. A low molecular weight compound which induces or inhibits the expression of human BMP-7 can be obtained by isolating the promoter which regulates the expression of the gene, by connecting it to a suitable reporter gene and by introducing the gene structure to a suitable mammal cell to make an exploring system. The substance which regulates the expression of human BMP-7 in the exploring system works on the promoter to increase or decrease the expression level of the reporter gene. Therefore, a simple and easy measurement of the reporter activity makes an exploration of the aimed substance possible.

The animal cell transfected with said vector can be used for a method for screening a chemical compound library by high throughput screening (Nature, Vol. 384, Suppl., p. 14–16, (1996) and exploring an active substance from natural substances. The substance which increases or decreases an activity is searched by treating the cell with a substance for an appropriate time period and thereafter measuring the reporter activity. The substance obtained hereby can regulate the expression by working directly on a transcription factor or indirectly on the promoter of human BMP-7 through regulating a signal transduction system. Therefore, these compounds are effective as a therapeutic agent for osteocartilaginous diseases, cancer metastasis to bone, or osteohyperplasia.

Furthermore, these compounds are useful as a therapeutic agent for kidney disorders.

The substance obtained by the present invention has bone or cartilage morphogenetic activity and is effective as an agent for therapeutic and preventive treatment in the fields of orthopedic surgery (fracture, osteoarthritis such as joint osteoarthritis and hip joint osteoarthritis, arthrosteitis, damage of cartilage such as damage of meniscus, regeneration of bone and cartilage deficit caused by injury and tumor dissection, bone reconstruction such as spinal fusion and vertebral canal enlargement, and congenital cartilage and bone diseases such as dysoteogenesis and achondroplasia), or dental fields (bone reconstruction such as palatoschisis, mandible reconstruction, and residual ridge construction), and osteoporosis. Moreover, the substance of the present invention can be used for bone graft in aesthetic surgery. These therapeutic treatments are effective to therapies in the fields of veterinary surgery. On the other hand, the present invention can provide a substance to inhibit bone or cartilage morphogenesis. In this case, the substance is applied as an agent for prevention and therapy of bone and cartilarge hyperplasia.

In addition, the present invention can provide a substance with ability to enhance the differentiation of kidney cells and it can be applied to an agent for the treatment and prevention of the kidney disorder.

EXAMPLES

This invention shall be more illustratively explained by way of the following Examples. The following Examples are to be considered in all respects as illustrative and not restrictive.

Example 1

Isolation of 5' Upstream Region of Human BMP-7 Gene

A human placenta genomic DNA (a product of CloneTech) was digested by using various kinds of restriction enzymes (BamHI, BglII, EcoRI, HindIII, PstI, SacI, SalI, SmaI, SphI, and XbaI), separated by agarose gel electrophoresis, transferred to a nylon membrane, and subjected to the Southern hybridization using BMP-7 cDNA (EMBO J. 9: 2085–2093, 1990) as a probe. As the result, it was found that digestion by the restriction enzyme HindIII among restriction enzymes used yielded a DNA fragment of ca. 11 kb containing the longest human BMP-7 gene. Then, a human placenta genomic DNA was digested by the restriction enzyme HindIII and separated by agarose gel electrophoresis to extract a DNA fragment of ca. 11 kb from the agarose gel. The DNA fragment obtained was cloned to lambda phage vector λDASH II (Stratagene Ltd. made) digested by the restriction enzyme HindIII. The vector was in vitro packaged by Gigapack III XL Extract (Stratagene Ltd. made), infected to *Escherichia coli* XL1-Blue MRA (Stratagene Ltd. made) to make a genomic DNA library. The library was divided into pools. Each pool was amplified by a screening (Nucleic Acids Res. 21: 2627–2631, 1993) using PCR; namely, the PCR method by using PCR primers (SEQ ID NO. 2 and SEQ ID NO. 3 of the Sequence Listing) corresponding to translation region to select the objective pool, to obtain finally 5' upstream region (10.8 kb) of human BMP-7 gene. In addition, the 5' upstream 10.8 kb fragment was subcloned to a pUC18 vector (a product of Amersham Pharmacia Biotech). The vector was named *E. coli* pKOT 314. The *E. coli* pKOT 314 was deposited in National Institute of Bioscience and Human-Technology, Agency of Industrial Science and Technology, Ministry of International Trade and Industry 1-3, Higashi 1-chome, Tsukuba-shi Ibaraki-ken 305-8566 Japan, in Mar. 30, 1998 with depository number FERM P-16737 and transferred to the International Depository Authority under Budapest Treaty on Feb. 17, 1999 (Deposit No. FERM BP-6651).

Example 2

Determination of DNA Sequence of 5' Upstream Region of Human BMP-7 Gene

The sequence of 5' upstream region of human BMP-7 gene obtained was determined by Amersham Pharmacia Biotech's ALF DNA Sequencer according to the method of Sanger et al. (Proc. Natl Acad. Sci. USA 74: 5463–5467. 1977). The sequence thus analyzed is described in SEQ ID NO. 1 of the Sequence Listing. The base sequence No. from 5557 to 10780 of SEQ ID NO. 1 was already been reported (EMBO J. 9: 2085–2093, 1990). However, there are many differences from the sequence of this invention.

Example 3

Figure 1:
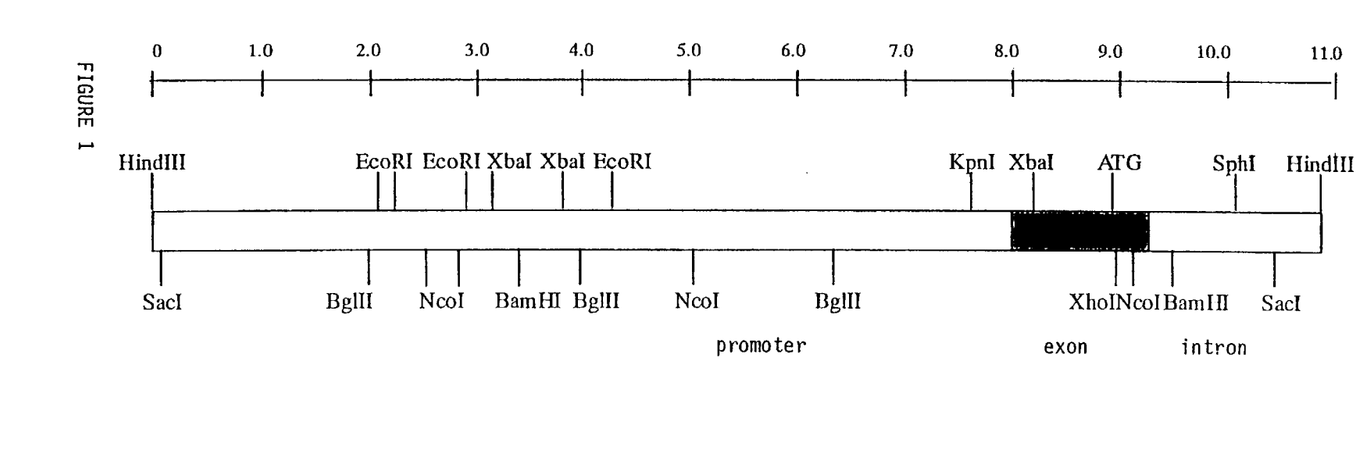
FIG. 1 is an exon-intron structure of 10.8 kb 5' upstream region of human BMP-7 gene and a restriction enzyme map. A net shape shows an exon region and an open square shows an intron region.
Figure 2:
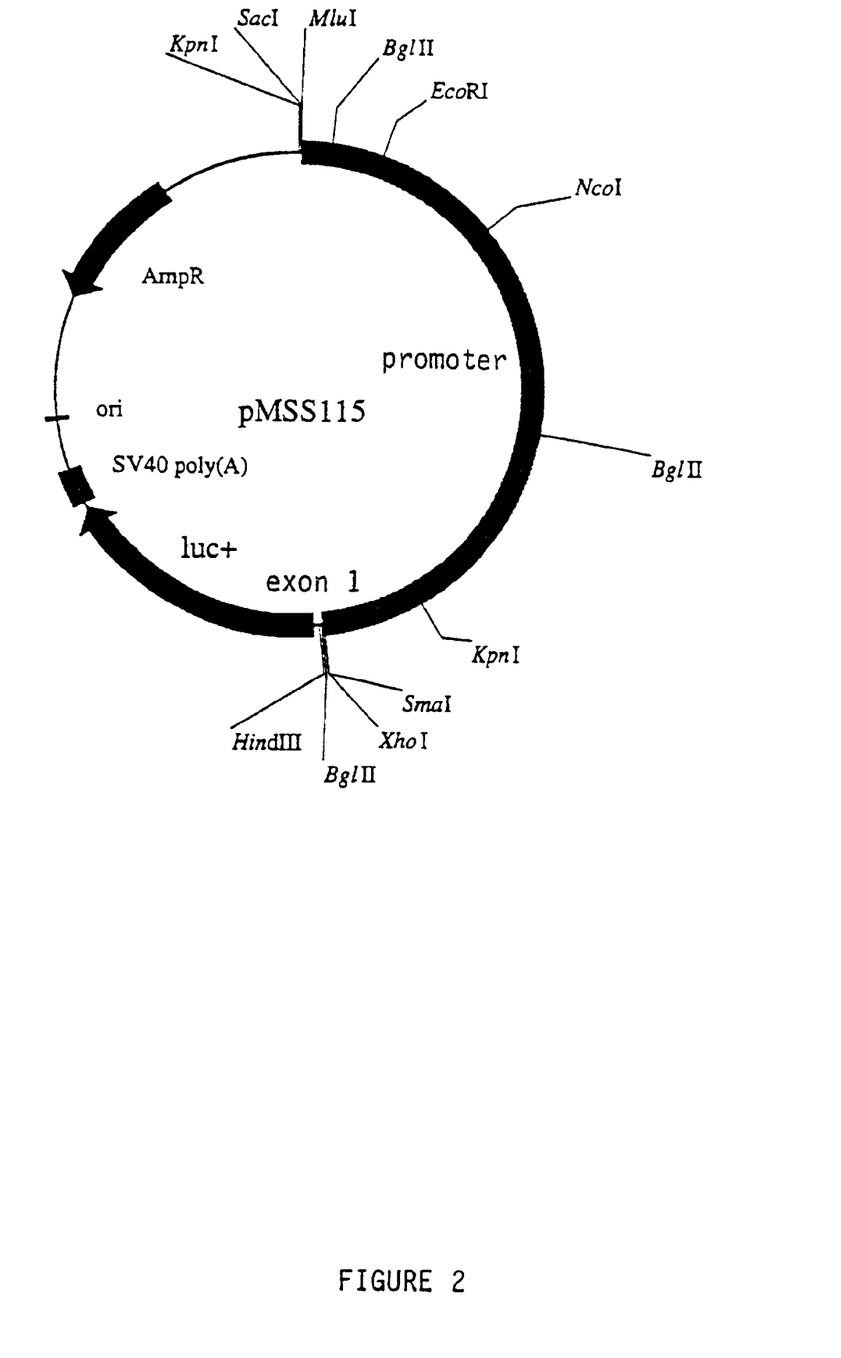
FIG. 2 is a recombinant expression vector (pMSS115) containing a 5' upstream region of human BMP-7 gene. A promoter region (4.4 kb) (base No. from 3813 to 8222 shown in SEQ ID NO. 1 of the Sequence Listing, referring from the 2nd XbaI to the 3rd XbaI from 5' terminal in FIG. 1) was inserted to NheI restriction enzyme site of pGL3-basic.

Construction of a Recombinant Expression Vector Containing the Human BMP-7 Promoter and a Luciferase Reporter Gene As shown in FIG. 1, the promoter of human BMP-7 exists in the upstream of exon 1. Then, a region of 4.4 kb containing a promoter from XbaI of the second position to XbaI of the third position from the 5' terminal described in FIG. 1 were—to align in the upstream of the reporter gene-inserted in the restriction enzyme site, NheI, of a luciferase reporter vector pGL3-basic (a product of Pro Mega Ltd.) to construct a recombinant expression vector pMSS115 (9.2 kb). This is presented in FIG. 2.

Example 4
Measurement of the Activity of the Human BMP-7 Promoter (Introduction of a Recombinant Expression Vector to a Human Cell and Transient Expression)

Figure 3:
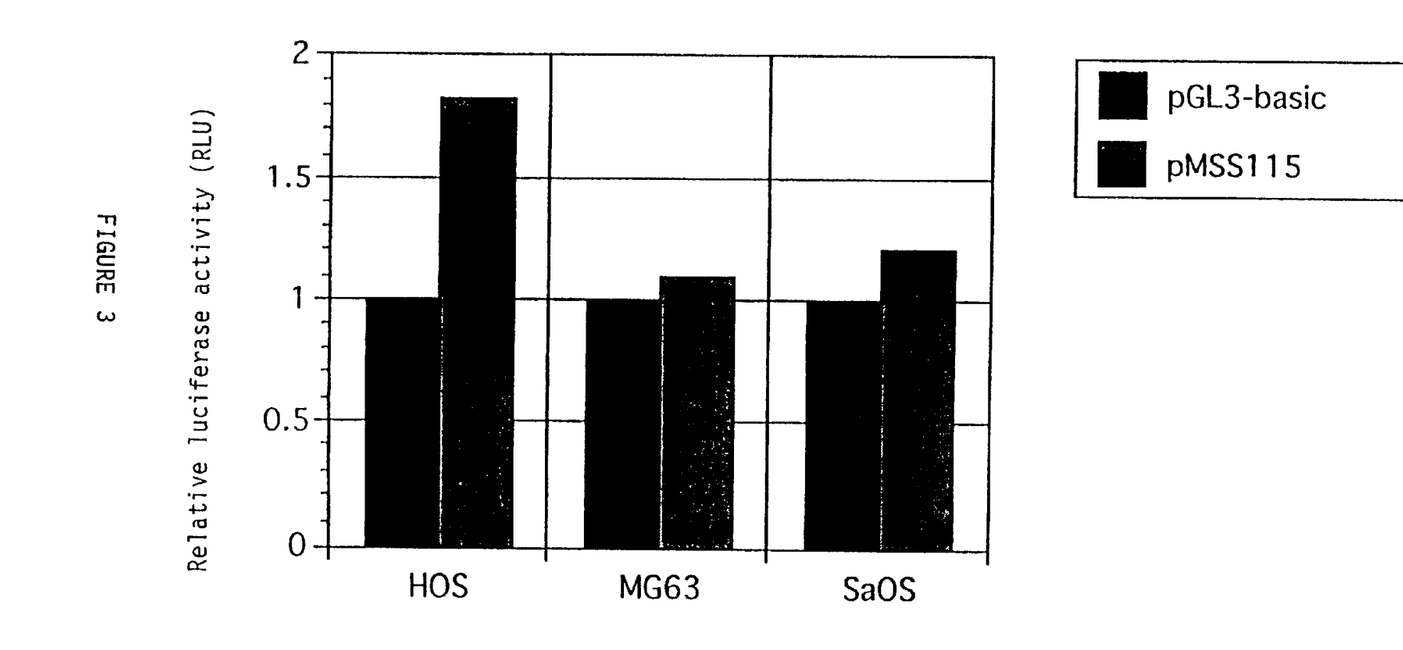
FIG. 3 is a result of measuring human BMP-7 promoter activity (transiently expression).

In order to express transiently the human BMP-7 recombinant expression vector, said recombinant expression vector (pMSS115) was mixed with a vector, pRL-SV40 (a product by Pro Mega Co.) containing sea pansy luciferase gene as an internal control for measurement of efficiency of gene introduction in equal quantity. Then, cationic liposome lipofectamine (a product of Lifetech Oriental Co.) was added to the mixture solution to add to human osteosarcoma cells HOS, MG63, and SaOS-2 for transfection. Fire fly luciferase activity and sea pansy luciferase activity were measured by Pikka Gene Dual Kit (a product of Toyo Ink Co.). The result is presented in FIG. 3. The promoter activity was expressed as a ratio of fire fly luciferase activity to sea pansy luciferase activity. From the result, it has been known that the DNA of SEQ ID NO. 1 of the Sequence Listing has a promoter activity.

Example 5
Introduction of the Recombinant Expression Vector to a Human Cell and Stabilized Expression In order to express the human BMP-7 recombinant expression vector stably, said vector was mixed with a vector pPUR (a product of CloneTech Ltd.) containing puromycin resistant gene in the proportion of 10:1 and also mixed with cationic liposome lipofectamine (a product of Lifetech Oriental Co.) to add to a human osteosarcoma cell HOS for transfection. The cells to which the aimed gene had been introduced were selected from a culture medium containing puromycin (a product of Sigma Ltd.).

Example 6
Screening of Active Low Molecular Weight Compound

The established cells selected were inoculated in a 96-well plate, treated with substances of various chemical compound libraries for 1–3 days, dissolved with a cytolytic agent (a product of Pro Mega Ltd.), and measured for enzyme activity by employing a luciferase assay kit (a product of Pro Mega Ltd.). By such processes, various substances inducing or inhibiting the expression of human BMP-7 are obtained.

Sequence Listing Free Text

<210> 1
  <223> Human BMP-7 5' upstream gene sequence including the exon 1 regions.
<210> 2
  <223> Sense PCR primer for cloning 5' upstream human BMP-7 gene sequence corresponding to the exon 1 region.
<210> 3
  <223> Reverse PCR primer for cloning 5' upstream human BMP-7 gene sequence corresponding to the exon 1 region.

SEQUENCE LISTING

<160> NUMBER OF SEQ ID NOS: 3

<210> SEQ ID NO 1
<211> LENGTH: 10877
<212> TYPE: DNA
<213> ORGANISM: HUMAN
<220> FEATURE:
<221> NAME/KEY: misc_feature
<222> LOCATION: (1)..(10877)
<223> OTHER INFORMATION: Human BMP-7  5' upstream gene sequence
      including the exon 1 regions.

<400> SEQUENCE: 1
aagcttggac atcagatagc tgtgtcattc atgctaactc ttattagttg ttgcatcata      60
tgtaagatga gctcaaatct gttaatcttc ccatacgatc tttcacatg agttgggact     120 aacctgttat atttagagta atggtttacc aatggggagg gaataaagat aaaactcgaa     180
gtaaaagaaa gaatacaatt ttttaaatga ggagaaacac agtgaaggag aggagagaag     240
gaagaaaaca acagagatgg agagaagcac gacgtggggt ggtgaggagt tcccaggact     300
ctgggagcga ggagcccagt ctaatccctg attcactgta agactttggg cccagcagtt     360
tctctttggg tgtcaatttc tctatcttca agatgaagga attgaaccac gcttctgcag     420 gactttgtt gtaactgact ggaaactccg tacacaatgg cttaaactga acagtcctgg     480
gtggggctgg cttcagggat agtgggctcc aggggctcac tgatgctgtc agtctcctgc     540
cttttcttgt tttactgtct tgtggcttct ctcacagggc aggctctccc tgaagggagg     600

-continued

| | | | |
|---|---|---|---|
| gaagatgaca | gccagcagca | gcccctgacc | tagcaacccc agtgggagga gagacccctt | 660 |
| taccggtagt | tctagcaaaa | gttctaaaag | ttgaatctca ctggcctgga ttaggtcaca | 720 |
| tgactgtcac | tgaacccatc | gcatgggcat | ctctggttga ccaggctggg tcatgtgccc | 780 |
| agtctgaatt | ttagagaaga | ggatagttca | acctgaaata cagggactga tggtgaagaa | 840 |
| ggggcatttc | tactgaggaa | acagaggaa | atccttggcca ggcacagtgg cttatgcctg | 900 |
| taatcccagc | actttgagag | gccaagatgg | atggattgtt tgaggcccgg agttcaagac | 960 |
| cagtctggcc | agcgtggtgt | aaccctgtct | tctactaaaa atacaaaaat tagccaggca | 1020 |
| tggtggtgca | cacctgtaat | cccagctact | cgggggggct gaggagggag aattgcttga | 1080 |
| aaccgggagg | cagaggttac | agtgagctga | gattgtgcca ttgcactcca gcctgggtga | 1140 |
| cagagggaga | ctctgtctaa | aaaaaaaag | aaaagaaaag aaaacagagg aaatatttgc | 1200 |
| agaagaagga | gaaaaggcag | gggtctcaaa | ttaggtgagc ttccaaagtg ttttctgtgg | 1260 |
| aaccctggga | gcagagaaaa | tggtagtgaa | aagaaacagg cctggggact ctgggcccct | 1320 |
| gctgggatca | cctgataaca | ggcagggtgt | ccagtccgat ttgaacttca gataaacaac | 1380 |
| gagtaaattt | cagtatgagt | atatataata | catatactcc aatataatgg gatatagtca | 1440 |
| tactaaaatt | cattcattgt | ttatctgaaa | ttcaaattga actggacacc tatttttttt | 1500 |
| tttgcaaaat | gtggtaaccc | tagtccctcc | cctgctctat gtaaccaaag aagctctgtt | 1560 |
| tctgttttct | gtgtcgagca | tgtgtgaaaa | actccttgac caaagttttt agcgctgcac | 1620 |
| aaaagagaag | gcctgtatcc | ttttaactga | catgattgcc atgccctctc cagctcccca | 1680 |
| gtgctgtatc | cagcagggct | tctggctgca | ggcaacagaa accagcttgg gcaggctggt | 1740 |
| gcggaaaagg | agaccactag | aggatcttgg | gggctcacag aaccctggg aaggccagag | 1800 |
| aaccaggctt | gggggctctc | tagttgggac | acggccccag atcactctgc agaatagtct | 1860 |
| gggcctgcac | tgatagcttc | tggggtgggt | gcctctgact ggctgaaact tggtcacctg | 1920 |
| tcagggctct | ggctgcaaag | caggctagac | agtgcctctc tggatattca ccagatgggg | 1980 |
| catcctcaac | cataagagag | ggctcagatc | tagctgggag gagggagatg ctgaaaagca | 2040 |
| ggagcaatga | acactcactc | ctgctcttgc | agatggaatt ctggttttg atgtttctcg | 2100 |
| ggagaggggg | agtttatcag | atcagtcacc | agggccaaac agcagagttt tgctgggaag | 2160 |
| ggactctggg | gaaggttagg | gtcagatttt | gcctaaaggg gcagacagtt ccagcctttt | 2220 |
| caaccactgg | ctcagtagcc | ctcgaatcat | gaattcaatg gagctgtctt gaaatgcacc | 2280 |
| atccttggtg | gtcctttggt | ttgggtgatg | ggttggggga ggctgggcac atcctccaga | 2340 |
| cacagcagag | ccctttatga | ggccaggggc | aaaccagatt catcgaatct gactggtaga | 2400 |
| tgtgtcttct | ttggtctaat | aaccaaaacg | agttgaatta gttgccaaca gataaacatt | 2460 |
| gagagatgtc | acattcaaac | tcaagtttct | agcttctttg gaaaatcaga actttctggt | 2520 |
| gatgttggaa | tcaaatttct | ggatggcatc | acccatgggc atgtggtttc cagttcaccc | 2580 |
| cagtctgcac | cctccttatt | tatccaggcc | agtgtctcct gccacctgtc accatgtctg | 2640 |
| tgctcatgat | tgccttccat | taaattaaga | ggaagagaaa tattccttga gcttcatgtt | 2700 |
| gcatctctgt | atttatgtta | cctgttggt | gcccgttggc ttttgagtgt atgacttctg | 2760 |
| caataaagga | ggaattgaag | aagggctcag | aggtatgttc ctcaaacact gatagggcat | 2820 |
| ctactgtgtg | caaggcctcc | atgggtactg | ggaggtccct acaggactaa acaaaccct | 2880 |
| gtgttttggt | gtacctcaat | gtttaaggac | ttaagtcctg gaacaagata gccggcgtca | 2940 |
| gaattctgat | tttaccattc | actcaccatt | ggtgtggctt tgggcaggtt ccctcaagta | 3000 |

-continued

```
tttgagcctc aatttcctca tctgtaaaat ggggataata ataataaaaa tcatacaagg    3060
tagttgggag aattaatgag ttaattttaa aagacacctg gaatcataga tattgaagtt    3120
ttaatttgaa gccccaattt gtcagctata acttcagaaa tctagagcct cgatcgtcaa    3180
catacagcct gaagacgaca gcctccgagc ccccaggag ctagttagaa gtgcagaatc     3240
tcagctcact cagactgact gtgggaatct atgttctaac agaccccag gggattcaca     3300 cgcacagttg ggttggagaa gtgttgcttt aggttaaagc aaggaaggaa ggggctgctc    3360
ccaggtcact gaacgtgcac tgatgcttaa aggcctgggc tgtgtagaca gatgtggctt    3420
tggatcctgg ctccattaca gattagattg gctgtctgac tctggacaag gtgctctcgg    3480
gatgttggtc ctcctctgca atctgaggag cagaactagc ctctccatgc agtggggagt    3540
tgcgggtgat gtgggcttgg gccgtgcagg cctagcaggt gcccagcaga agcaagtgct    3600
cccaacaggt gacaggtcgg ccgctcccct gtcacgtttt ggaaggagga aagggctacc    3660
tctagtgctg aaccgaggat agttagtgct caaaaccata ccagatttcc tccaatcaag    3720
gaagaaataa cagccctgat aataataaac aaaaccactg cttcccccta gctggcttcc    3780
agatcctaga aatcctgcat ggtatcagct tctctagagt gtgtgtgtcg tctgtatttt    3840
ccatttggaa ctgtggccac tgccatgtgt acttaagact gatggaagac gtttaatctc    3900
ttattctgct gcttttaaag ttgtgcaaag aaaatctcag agtgggcaag cgtgaggagt    3960
ccaagcctcc cgtgcaatga gagatctgcg tgggaaacaa aatttcacca caggtgtgct    4020
ctaataattt cctctgcagg gtccacctct gcacacaacg attttcaagc ctgtgcagga    4080
ggcagctctt ggccctctat tccttgttgg ggttggaggt ccaggtcatc tggcctttgc    4140
caggtggtgt ggacagagag agagcagccc actggcttcc ttggctgtgc tccccaggga    4200
gcttccaggc cagctgagcc tcctctaggg cagatggatg aagatgaggt ccccacctcg    4260
ctgaacaatg tgtgtgtcag cagaattctt ttcttctttt tactgcctta gagagacatg    4320
ctgacttggt caaaatcact tcagcaagat gtgactgatg atgtaggaaa tgaaaactcc    4380
tggcccagca ctgggaggcc agcaggcgag gggcgcggac actgggaccg gccacccga     4440 cacaataaca ccccttacaa ttccaggccg tctttcatcc aggcaaaggc ggccccaggt    4500
gtggagcaga ctggggcaga tcagattacg gtcctggagc ccagtgctgg gtgccctggc    4560
caggggaacc acaactgggg gtgtgtgggt tgggggctag ctgctgggga aatgagatag    4620
gacccaggga agtccctggg ccccagctgg cctgcagggg gcctaggcac aatgtgagga    4680
ttggaatgca gtgatgacct tttcatctct catgttccct tccacttcac tctctctttt    4740
gctctggtac ttttgctctt gctctcagag tcaggataca tctgcttttc tctgcttggc    4800
aaaaagcaga ccatcatgaa aagttttgtt gtaatttgaa actcaggagg ctttcctgtt    4860
accatatttt cctttttcatc cagatggtaa cacaataaca tttatcaagg gttttctctg    4920
tgttccaggc actgtgcaaa gccctttcca tgaattaagt tctgcaacct cacagcgatc    4980
ccagaagaca ggcgctatca gtcccccat tttacagatg ggggaactga ggtgtagaga     5040
ggttaagtcc cttgcccatg gtgcacagct ggaagagaca gagctggagt gtgaatgcgg    5100
ctgggcaggc tccagtgccc aggctacctc ctccacacaa gacttgccct cggcaatctc    5160
aaagcctttt ctggtggtgg gctcagctcc caaactggca tcggatgcac tcccagccag    5220
atatttcttg cttccggtt ttcattcatt cattcattca ttcattcatt cattcattcg     5280
gcattcactg agggcctggt gcagtcttgg ggatgcctct cggggaggaa acagggaaaa    5340
```

-continued

```
gaaagacccc cccaccaagc atggatcaca gaaaagataa ggctaaatgg gggtttgtgg    5400
gacttcagag gaaaccttat ctcttgaggt cttggatatg aagagcatgt tgtctcttcc    5460
tcttgcatga gaaagatgg cgtctcagag gaagggttgc tggggtgagg gatctgggag     5520
atgccttagc ttggcgcctg cacagtcagc cctcagtcaa ccggtctctt taggttttgg    5580
ctgtgcttat tactattcat tcaacaggta ctaattgagc acctgctgtg tgccaggctc    5640
agaataggct caggtgagat gcacaaagaa gggtaaacta gaatccttgc ttagacactg    5700
acggatcagt tgtttcatat gtaaattgta gcaccaagac ctgctgcccc tgcccccagc    5760
ctcacctgct tgtgaagatc cctccaaaag atttgagagt agataaaaag cagagactac    5820
tactgaagaa cagggctgct ttggctcctt attatttcag actttggaag aaaatgacct    5880 ccttttctc tactggcact ggaggtggca tagctgtccc tagcaagcca gcgctggagg     5940
gcgtgtgcag ggctggggac cgagcctggt ttctgttccc tgctctgcag gctcaagcac    6000
ttgctgttcc tccacctggg atgcctttcc ctggaaaagc ctgtctcttt cttgtctttc    6060
aggactcagg tcagtggcat ctcctccaaa aactcccctt cccaccctcc atcacctcac    6120
cctgtttatc tgcgcccccg cccccactgc ctgtcactta ttgcaggctg aagtgaccca    6180
ggctctccag ttgtacactc tcagatggac cctggacgac tgtggcactc ctgcaatttc    6240
cccagtctcc ctggggtagg attcctgctt gccaggatgc ccacctttcc ttctccctcc    6300
tgcatgtcct cctctgcctg gcttctgaat tgttcccaga gagagtgata gacaagatct    6360
gcctctcctt cagtccctga atcttattta aggctcttgc tttgcttccc tggcctggag    6420
gcggctcctt gatggagtct gccatgtggg ttcgctcatg gccatgtctt cctgcccagc    6480
atggtgcttg gccctgggac tggccacata atatctgggc caggtgcaaa attagtacgg    6540
ggcagggggt actttgttca taggtgattc agaaccacat atggtgacct cagagtagga    6600
aaccaagtgt ggggccctta agagctgggg ggccctgtac gactgtccag gttgcaggcc    6660
ccacagctcg cctcctgata tcctgtgctc catgcttgtc tgttgaagga aggagtgaat    6720
ggatgaagag caggtggtgg gggtggtttg agggccttgc tggtgggtgg gtagaggccc    6780
ctccctggca tggggctcaa gacctgttcc atcccacagc ctggggcctg tgtgtaaatg    6840
gccaggacct gcaggctggc atttttctgc tccttgcctg cctctggcct cccctttctc    6900
cacccatgtg gcccctcagg ttgccatcta gtccaaaagt ccccaaggga gacccagagg    6960
gccacttggc caaactactt ctgctccaga aaactgtaga agaccataat tctcttcccc    7020
agctctcctg ctccaggaag gacagcccca agtgaggct tagccagagc ccctcccaga     7080
caagcgcccc cgcttcccca acctcagccc ttcccagttc atcccaaagg ccctctgggg    7140
acccactctc tcacccagcc ccaggagggg aaggagacag gatgaacttt taccccgctg    7200
ccctcactgc cactctgggt gcagtaattc ccttgagatc ccacaccggc agagggaccg    7260
gtgggttctg agtggtctgg ggactccctg tgacagcgtg catggctcgg tattgattga    7320
gggatgaatg gatgaggaga gacaggagag gaggccgatg gggaggtctc aggcacagac    7380
ccttggaggg gaagaggatg tgaagaccag cggctggctc cccaggcact gccacgagga    7440
gggctgatgg gaagccctag tggtgggct gggtgtctg gtctcaggct gagggtggc      7500 tggaaagata cagggccccg aagaggagga ggtgggaaga acccccccag ctcacacgca    7560
gttcacttat tcactcaaca aatcgtgact gcgcacgtac agtggctacc aggcgctggg    7620
ttcaaggcac tgcgggtacc agaggtgcgg agaagatcgc tgatccgggc ccagtgctc    7680 tgggtgtcta gcggggtaa gaaggcaata aagaaggcac ggagtaactc aaacagcaat    7740
```

```
tccagacagc aagagaaact acaggaaaga aaacaaacgt gcgagggggcg aggcgaggaa    7800 acaacctcag cttggcaggt cttggaggtc tctgggagga gaaagcagcg tctgatgggg    7860
gcgggaggtg gtgagtgggg agaggtccag gcggagggaa tggcgagcgc agagacaggc    7920
tggcaacggc ttcagggagg cgcggagggg tcagcgtggc tggcttaaaa ggatacatgg    7980
gactgagggg caagaccggc tcaagggtca ccgcttccag gaagccttct atttccgcgc    8040
caacctcggc gctcccccaa cttttcccac cgcggtccgc agcccacccg tcctgctcgg    8100
gccgccttcc tggtccggac cgcgagtgcc gagagggcag ggccggctcc gattcctcca    8160
gccgcatccc cgcgacgtcc cgccaggctc taggcacccc gtgggcactc agtaaacatt    8220
tgtcgagcgc tctagaggga atgaatgaac ccactgggca cagctggggg gagggcgggg    8280
ccgagggcag gtgggaggcc gccggcgcgg gaggggcccc tcgaagcccg tcctcctcct    8340
cctcctcctc cgcccaggcc ccagcgcgta ccactctggc gctcccgagg cggcctcttg    8400
tgcgatccag ggcgcacaag gctgggagag cgccccgggg ccctgctat ccgcgccgga     8460 gttggaagag ggtgggttgc cgccgcccga gggcgagagc gccagaggag cgggaagaag    8520
gagcgctcgc ccgcccgcct gcctcctcgc tgcctccccg gcgttggctc tctggactcc    8580
taggcttgct ggctgctcct cccacccgcg cccgcctcct cactcgcctt tcgttcgcc     8640 ggggctgctt tccaagccct gcggtgcgcc cgggcgagtg cggggcgagg ggcccggggc    8700
cagcaccgag caggggcgg gggtccgggc agagcgcggc cggccgggga ggggccatgt     8760
ctggcgcggg cgcagcgggg cccgtctgca gcaagtgacc gacggccggg acggccgcct    8820
gccccctctg ccacctgggg cggtgcgggc ccggagcccg gagcccgggt agcgcgtaga    8880
gccggcgcga tgcacgtgcg ctcactgcga gctgcggcgc cgcacagctt cgtggcgctc    8940
tgggcacccc tgttcctgct gcgctccgcc ctggccgact tcagcctgga caacgaggtg    9000
cactcgagct tcatccaccg gcgcctccgc agccaggagc ggcgggagat gcagcgcgag    9060
atcctctcca ttttgggctt gccccaccgc ccgcgcccgc acctccaggg caagcacaac    9120
tcggcaccca tgttcatgct ggacctgtac aacgccatgg cggtggagga gggcggcggg    9180
cccggcggcc agggcttctc ctaccccta aaggccgtct tcagtaccca gggcccccct    9240
ctggccagcc tgcaagatag ccatttcctc accgacgccg acatggtcat gagcttcgtc    9300
aacctcggtg agtaagggca ggcgagggta cgcgtctcct ttcggggca ctttgagact     9360 gggagggagg gagccgcttc ttctatgcag cccgcccagc tttccgctcc tggctgaaat    9420
cgcagtgcct gccgagggt ctcccaccca cagccctatg actcccaagc tgtgtgcgcc     9480
cccaggtcgg gcgcgctggg ttcggtgagc ctgtaggggt tactgggaag gagggatcct    9540
ccgaagtccc ctccatgtta cgccgccggc cgcatctctg gggctggagg caagggccgt    9600
tcaaagcgcg gggctcggtc atgtgagctg tcccggccg gcgcggctcg cgtaacctgg     9660
atgtaaaggg cccttcccgg cgaggctgcc ttgccgccct tcctgggccc ctctcagccc    9720
tgcctggccc tggcatcgcg gccgtcgcac ccccttaccc tccctgtcaa gcctacctg     9780 tcccctcgtg gtgcgcccgc cttagcgtac cgcgcgctcc gagcgcttgg ggcccctctc    9840
cgggccgccg gatgccccat tctctcttgg ctggagctgg ggaagaaacg gtgccattgc    9900
taattttctt tgttttcttt ctttgtttat tttttttctt ttttcttttt tttcttttc     9960 ttttcttttc tttttttttt tttttgaga cggagttcac tcttgtcgcc cagtctggag    10020
tgcaatggcg cgatctctgc tcaccgcaac ctctgcctcc cgggttcaag cgattctcgt    10080
```

```
gcctcagcct cccgagtagc tgggattaca gcatgcgcca ccatgcctgg ctaattttgt  10140
atttttagta gagacagggt ttctccatgt taggcaggct ggtctcgaac tcccgatctc  10200
aggtgatcct cccgcctcag cctcccaaag tggtgctggg attacaggcg tgagccactg  10260
tgccctgccg ctagtcttct attttaagta tttagtggta ggtcccgggc cggcagaatc  10320
tattttcagc atttaccacg tgtggcgcgc aaaccacagg ttttggcgat tgggttgcgc  10380
gggatctcag actgacgcgc ggggcggct ggggtcccg gtttccgact ggagccgcga  10440
cgaccccggc gacgcgagcc tggggctgca gcgagggccg gggagctccc cctccatatg  10500
tgcgcgcaca ttctccagac ttgctcaaac taacccccg cggcgccagc gcgctgcggg  10560
actgatgatc aaatatttgg tttccgagat aacacacccc gatagcgctg tttcctgagc  10620
cgctttcatt ctacttgtgt aacttgctgc gaaaacccga accaagtcaa gacagcaaac  10680 tcacccacg ggcgctgtgt caacatgaa ataatgatac tgaagcccca cgctgggcac  10740 ctgggcgtg gactggggc gcggggaag cgcagatccg ccttcatgct tccccctcc  10800 tgataaggtc cctggagttc ccgggaggcc attgtctgta cttaataata actaaatcca  10860
actagtgaac caagctt                                                 10877

<210> SEQ ID NO 2
<211> LENGTH: 30
<212> TYPE: DNA
<213> ORGANISM: HUMAN
<220> FEATURE:
<221> NAME/KEY: misc_feature
<222> LOCATION: (1)..(30)
<223> OTHER INFORMATION: Sense PCR primer for cloning 5' upstream  human
      BMP-7 gene sequence corresponding to the exon 1
      region.

<400> SEQUENCE: 2
gggcgcagcg gggcccgtct gcagcaagtg                                   30

<210> SEQ ID NO 3
<211> LENGTH: 30
<212> TYPE: DNA
<213> ORGANISM: HUMAN
<220> FEATURE:
<221> NAME/KEY: misc_feature
<222> LOCATION: Complement((1)..(30))
<223> OTHER INFORMATION: Reverse PCR primer for cloning 5' upstream
      human BMP-7 gene sequence corresponding to the exon 1 region.

<400> SEQUENCE: 3
agaggatctc gcgctgcatc tcccgccgct                                   30
```

What is claimed is:

1. An isolated nucleic acid corresponding to SEQ ID No: 1 that encodes a human bone morphogenetic protein-7 promoter region.

2. A method for preparing isolated nucleic acid corresponding to SEQ ID No: 1 comprising
   (1) digesting a human placenta genomic DNA with a HindIII restriction enzyme,
   (2) isolating by agarose gel electrophoresis a DNA fragment,
   (3) cloning of the isolated DNA fragment digested with HindIII into a lambda phage vector λDASH II treated with the same enzyme,
   (4) inserting the said vector into the phage,
   (5) establishing a genomic DNA library by infecting *Escherichia coli* with the phage,
   (6) screening by PCR, and
   (7) subcloning into a plasmid vector.

3. A recombinant expression vector comprising the human bone morphogenic protein-7 promoter region of claim 1 operably linked and 5' to a reporter gene selected from the group consisting of luciferase and beta-galactosidase.

4. A method for identifying candidate compounds for inhibiting or inducing osteogenesis, which candidate compounds increase or decrease human bone morphogenic protein-7 promoter activity, comprising introducing the recombinant expression vector of claim 3 into a mammalian cell in vitro and measuring a change in reporter gene expression in the presence of said candidate compounds.

* * * * *